(12) United States Patent
Bedingham et al.

(10) Patent No.: US 6,720,187 B2
(45) Date of Patent: Apr. 13, 2004

(54) MULTI-FORMAT SAMPLE PROCESSING DEVICES

(75) Inventors: William Bedingham, Woodbury, MN (US); Barry W. Robole, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/837,073

(22) Filed: Apr. 18, 2001

(65) Prior Publication Data

US 2002/0001848 A1 Jan. 3, 2002

Related U.S. Application Data

(60) Provisional application No. 60/214,508, filed on Jun. 28, 2000, provisional application No. 60/214,642, filed on Jun. 28, 2000, provisional application No. 60/237,151, filed on Oct. 2, 2000, provisional application No. 60/260,063, filed on Jan. 6, 2001, and provisional application No. 60/284,637, filed on Apr. 18, 2001.

(51) Int. Cl.[7] ............................................. G01N 35/00
(52) U.S. Cl. ........................... 436/45; 436/177; 422/64; 422/72; 422/100; 435/288.4
(58) Field of Search ......................... 422/58, 100, 64, 422/72; 436/45, 50, 180, 177; 435/91.2, 305.1, 288.4, 809, 303.1; 219/388, 428, 438

(56) References Cited

U.S. PATENT DOCUMENTS

| | | | |
|---|---|---|---|
| 5,571,410 A | * | 11/1996 | Swedberg et al. .......... 204/451 |
| 5,593,838 A | * | 1/1997 | Zanzucchi et al. .......... 204/450 |
| 5,637,469 A | * | 6/1997 | Wilding et al. ................ 422/55 |
| 5,948,227 A | * | 9/1999 | Dubrow ....................... 204/455 |
| 6,013,513 A | | 1/2000 | Reber et al. |
| 6,030,581 A | | 2/2000 | Virtanen |
| 6,063,589 A | | 5/2000 | Kellogg et al. |
| 6,143,248 A | | 11/2000 | Kellogg et al. |
| 6,319,469 B1 | | 11/2001 | Mian et al. |

FOREIGN PATENT DOCUMENTS

| | | | | |
|---|---|---|---|---|
| EP | 0 169 306 A2 B1 | 1/1986 | | |
| EP | 0 693 560 A2 A3 | 1/1996 | | |
| WO | WO 97/21090 A1 | 6/1997 | | |
| WO | WO 9721090 A1 | * 6/1997 | ......... | G01N/21/07 |
| WO | WO 9909374 A1 | * 2/1999 | ......... | G01N/21/07 |
| WO | WO 99/09394 A1 | 2/1999 | | |
| WO | WO 99/55827 A1 | 11/1999 | | |
| WO | WO 99/58245 A1 | 11/1999 | | |
| WO | WO 99/67639 A1 | 12/1999 | | |
| WO | WO 00/05582 A2 | 2/2000 | | |
| WO | WO 00/40750 A1 | 7/2000 | | |
| WO | WO 00/50172 A1 | 8/2000 | | |
| WO | WO 00/50642 A1 | 8/2000 | | |
| WO | WO 00/69560 A1 | 11/2000 | | |
| WO | WO 00/78455 A1 | 12/2000 | | |
| WO | WO 00/79285 A2 | 12/2000 | | |
| WO | WO 200107892 A1 | * 2/2001 | ......... | G01N/15/06 |

OTHER PUBLICATIONS

Sambrook et al., *Molecular Cloning, A Laboratory Manual*, 2nd Edition, Cold Spring Harbor Laboratory, 1989.

* cited by examiner

*Primary Examiner*—Lyle A. Alexander
(74) *Attorney, Agent, or Firm*—Christopher D. Gram; Robert W. Sprague

(57) ABSTRACT

Devices, methods, and systems for processing sample materials are disclosed. The present invention may provide a bridge between standard microtiter plate systems, methods, protocols, etc. (that include wells arranged in rectangular arrays) and rotating sample processing devices and systems that allow users to obtain the rapid processing advantages of the more advanced sample processing devices. The sample processing devices preferably include a rectangular body to improve compatibility of the sample processing devices of the present invention with equipment designed for use with more conventional microtiter plates (which are typically rectangular in shape). The sample processing devices also include at least one set of process chambers arranged in one or more circular arcs and may include input and/or output chambers arranged in a rectilinear grid array.

29 Claims, 7 Drawing Sheets

MULTI-FORMAT SAMPLE PROCESSING DEVICES

RELATED APPLICATIONS

This application claims the benefit of the following applications: U.S. Provisional Patent Application Ser. No. 60/214,508 filed on Jun. 28, 2000 and titled THERMAL PROCESSING DEVICES AND METHODS; U.S. Provisional Patent Application Ser. No. 60/214,642 filed on Jun. 28, 2000 and titled SAMPLE PROCESSING DEVICES, SYSTEMS AND METHODS; U.S. Provisional Patent Application Ser. No. 60/237,151 filed on Oct. 2, 2000 and titled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METHODS; and U.S. Provisional Patent Application Ser. No. 60/284,637 filed on Apr. 18, 2001 and titled ENHANCED SAMPLE PROCESSING DEVICES, SYSTEMS AND METHODS—all of which are hereby incorporated by reference in their entireties.

FIELD OF THE INVENTION

The present invention relates to sample processing systems and methods. More particularly, the present invention provides devices, methods, and systems for processing sample materials.

BACKGROUND

Many different chemical, biochemical, and other reactions are sensitive to temperature variations. The reactions may be enhanced or inhibited based on the temperatures of the materials involved. Although it may be possible to process samples individually and obtain accurate sample-to-sample results, individual processing can be time-consuming and expensive.

Examples of some thermal processes that may be sensitive to temperature variations include, e.g., the manipulation of nucleic acid samples to assist in the deciphering of the genetic code. See, e.g., T. Maniatis et al. *Molecular Cloning, A Laboratory Manual*, Cold Spring Harbor Laboratory (1982). Nucleic acid manipulation techniques include amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR). Other examples of nucleic acid manipulation techniques include, e.g., Sanger sequencing, ligand-binding assays, etc.

One approach to reducing the time and cost of thermally processing multiple samples using such techniques is to use a device including multiple chambers in which different portions of one sample or different samples can be processed simultaneously. Although widely accepted standardized systems have been developed using microtiter plates having, e.g., 96, 384 or more wells arranged in rectangular arrays to speed the processing of multiple sample, even faster sample processing is still desired.

One disadvantage of many devices designed to provide faster processing is, however, their non-standard format as compared to, e.g., the widely accepted standard microtiter plates including wells arranged in rectangular arrays. As a result, it may be prohibitive in terms of, e.g., equipment costs, test result acceptance, etc. for a facility to abandon the industry standard processes completely and adopt a new test methodology and new equipment.

SUMMARY OF THE INVENTION

The present invention provides devices, methods, and systems for processing sample materials that may be presented in a standard microtiter plate. More particularly, the present invention provides a bridge between standard microtiter plate systems, methods, protocols, etc. (that include wells arranged in rectangular arrays) and rotating sample processing devices and systems that allow users to obtain the rapid processing advantages of the more advanced sample processing devices.

The sample processing devices of the present invention preferably include a rectangular body to improve compatibility of the sample processing devices of the present invention with equipment designed for use with more conventional microtiter plates (which are typically rectangular in shape). Slight deviations from a true rectangle in the shape of the body are considered to fall within the scope of the present invention, although the body should have four identifiable corners at the junctions of four identifiable sides and two major surfaces. The sides need not necessarily form straight lines, although it may be preferred that the sample processing devices fit within the rectangular form factor of conventional microtiter plates.

The sample processing devices of the present invention include at least one set of process chambers arranged in one or more circular arcs such that the process chambers can be, e.g., located in contact with a circular thermal control ring. As a result, the sample processing device can be rotated during thermal cycling of the sample materials in the process chambers. Rotation of sample processing devices provides a number of advantages including, but not limited to assisting in the movement of sample materials between chambers in the sample processing devices and retention of sample materials in the desired chambers during processing (by virtue of the centrifugal forces acting on the sample materials during rotation).

Additional advantages of rotational processing including the facilitation of energy delivery to those chambers that are arranged in circular arcs by rotating the chambers such that they pass through a stationary beam of energy (e.g., laser energy, light, etc.). Those same advantages may also be available within the chambers arranged in circular arcs when employing detection methods in which the rotating chambers pass through a stationary detection system, e.g., a laser-based fluorescent detection.

Further, rotation of the sample processing devices may assist in thermal control of the sample materials by removing thermal energy using convection and conduction as air or other fluids move over the surface of the rotating sample processing devices.

The sample processing devices of the present invention also include input chambers and/or output chambers that are arranged on the sample processing devices in rectilinear grid arrays, thereby providing users with the ability to use equipment designed to process devices providing materials arranged in rectilinear grid arrays, e.g., microtiter plates, etc. For example, if the input chambers are arranged in a rectangular array, a conventional robotic pipetting tool may be used to deliver sample materials and/or reagents to the input chambers. Alternatively, or in addition to the rectangular arrangement of the input chambers, it may be possible to retrieve or monitor sample materials located in output chambers using conventional microtiter plate equipment if the output chambers are also arranged in rectangular arrays on the sample processing devices of the present invention.

In one aspect, the present invention provides a sample processing device including a rectangular body with a pair of opposing major surfaces and a center, a first portion, and a second portion, wherein the first portion and the second portion are located on opposite sides of the center; a plurality of first process arrays located within the first portion of the body, each of the first process arrays including an input chamber, an output chamber, and a primary process chamber located between the input chamber and the output chamber, wherein the primary process chambers of the plurality of process arrays are arranged in a circular arc about the center of the body; and a plurality of second process arrays located within the second portion of the body, each of the second process arrays including an input chamber, an output chamber, and a primary process chamber located between the input chamber and the output chamber, wherein the primary process chambers of the plurality of second process arrays are arranged in a circular arc about the center of the body.

In another aspect, the present invention provides a sample processing device including a rectangular body with a center, a first portion, and a second portion, wherein the first portion and the second portion are located on opposite sides of the center; a plurality of first process arrays located within the first portion of the body, each of the first process arrays including an input chamber, an output chamber, and a primary process chamber located between the input chamber and the output chamber, wherein the primary process chambers of the plurality of process arrays are arranged in a circular arc about the center of the body; and a plurality of second process arrays located within the second portion of the body, each of the second process arrays including an input chamber, an output chamber, and a primary process chamber located between the input chamber and the output chamber, wherein the primary process chambers of the plurality of second process arrays are arranged in a circular arc about the center of the body. The input chambers of the plurality of first process arrays and the input chambers of the plurality of second process arrays are arranged in rectilinear grid array; the output chambers of the first process arrays of the plurality of first process arrays are arranged in a rectilinear grid array; and the output chambers of the second process arrays of the plurality of second process arrays are arranged in a rectilinear grid array.

In another aspect, the present invention provides a sample processing device including a body with a center, a first portion, and a second portion, wherein the first portion and the second portion are located on opposite sides of the center; a plurality of first process arrays located within the first portion of the body, each of the first process arrays including an input chamber, an output chamber, and a primary process chamber located between the input chamber and the output chamber, wherein the primary process chambers of the plurality of process arrays are arranged in a circular arc about the center of the body, and further wherein the output chambers of the plurality of first process arrays are arranged in a rectilinear grid array; and a plurality of second process arrays located within the second portion of the body, each of the second process arrays including an input chamber, an output chamber, and a primary process chamber located between the input chamber and the output chamber, wherein the primary process chambers of the plurality of second process arrays are arranged in a circular arc about the center of the body, and further wherein the output chambers of the plurality of second process arrays are arranged in a rectilinear grid array.

In another aspect, the present invention provides a sample processing device including a body with a center, a first portion, and a second portion, wherein the first portion and the second portion are located on opposite sides of the center; a plurality of first process arrays located within the first portion of the body, each of the first process arrays including an input chamber, an output chamber, and a primary process chamber located between the input chamber and the output chamber, wherein the primary process chambers of the plurality of process arrays are arranged in a circular arc about the center of the body, and further wherein the input chambers of the plurality of first process arrays are arranged in a rectilinear grid array; and a plurality of second process arrays located within the second portion of the body, each of the second process arrays including an input chamber, an output chamber, and a primary process chamber located between the input chamber and the output chamber, wherein the primary process chambers of the plurality of second process arrays are arranged in a circular arc about the center of the body, and further wherein the input chambers of the plurality of second process arrays are arranged in a rectilinear grid array.

In another aspect, the present invention provides a sample processing device including a rectangular body and a plurality of first process arrays located within the body, each of the first process arrays including an input chamber, an output chamber, and a primary process chamber located between the input chamber and the output chamber. The primary process chambers of the plurality of process arrays are arranged in a circular arc and the input chambers of the plurality of first process arrays are arranged in rectilinear grid array.

In another aspect, the present invention provides a method of using a sample processing device, the method including providing a sample processing device that includes a rectangular body with a pair of opposing major surfaces and a center, a first portion, and a second portion, wherein the first portion and the second portion are located on opposite sides of the center; a plurality of first process arrays located within the first portion of the body, each of the first process arrays including an input chamber, an output chamber, and a primary process chamber located between the input chamber and the output chamber, wherein the primary process chambers of the plurality of process arrays are arranged in a circular arc about the center of the body; and a plurality of second process arrays located within the second portion of the body, each of the second process arrays including an input chamber, an output chamber, and a primary process chamber located between the input chamber and the output chamber, wherein the primary process chambers of the plurality of second process arrays are arranged in a circular arc about the center of the body. The method further includes loading sample material in the input chambers of at least some of the first and second process arrays; and transporting the sample material from the input chambers to at least some of the primary process chambers by rotating the sample processing device about an axis of rotation extending through the center of the body, wherein the primary process chambers are located further from the axis of rotation than the input chambers.

In another aspect, the present invention provides a method of using a sample processing device, the method including providing a sample processing device with a body including a center, a first portion, and a second portion, wherein the first portion and the second portion are located on opposite sides of the center; a plurality of first process arrays located within the first portion of the body, each of the first process arrays including an input chamber, an output chamber, and a primary process chamber located between the input chamber and the output chamber, wherein the primary process chambers of the plurality of process arrays are arranged in a circular arc about the center of the body, and further wherein the output chambers of the plurality of first process arrays are arranged in a rectilinear grid array; and a plurality of second process arrays located within the second portion of the body, each of the second process arrays including an input chamber, an output chamber, and a primary process chamber located between the input chamber and the output chamber, wherein the primary process chambers of the plurality of second process arrays are arranged in a circular arc about the center of the body, and further wherein the output chambers of the plurality of second process arrays are arranged in a rectilinear grid array. The method further includes loading sample material in the input chambers of at least some of the first and second process arrays; and transporting the sample material from the input chambers to at least some of the primary process chambers by rotating the sample processing device about an axis of rotation extending through the center of the body, wherein the primary process chambers are located further from the axis of rotation than the input chambers.

In another aspect, the present invention provides a method of using a sample processing device, the method including providing a sample processing device including a body with a center, a first portion, and a second portion, wherein the first portion and the second portion are located on opposite sides of the center; a plurality of first process arrays located within the first portion of the body, each of the first process arrays including an input chamber, an output chamber, and a primary process chamber located between the input chamber and the output chamber, wherein the primary process chambers of the plurality of process arrays are arranged in a circular arc about the center of the body, and further wherein the input chambers of the plurality of first process arrays are arranged in a rectilinear grid array; and a plurality of second process arrays located within the second portion of the body, each of the second process arrays including an input chamber, an output chamber, and a primary process chamber located between the input chamber and the output chamber, wherein the primary process chambers of the plurality of second process arrays are arranged in a circular arc about the center of the body, and further wherein the input chambers of the plurality of second process arrays are arranged in a rectilinear grid array. The method further includes loading sample material in the input chambers of at least some of the first and second process arrays; and transporting the sample material from the input chambers to at least some of the primary process chambers by rotating the sample processing device about an axis of rotation extending through the center of the body, wherein the primary process chambers are located further from the axis of rotation than the input chambers.

In another aspect, the present invention provides a method of using a sample processing device by providing a sample processing device that includes a rectangular body and a plurality of first process arrays located within the body, each of the first process arrays including an input chamber, an output chamber, and a primary process chamber located between the input chamber and the output chamber. The primary process chambers of the plurality of process arrays are arranged in a circular arc and the input chambers of the plurality of first process arrays are arranged in rectilinear grid array. The method further includes loading sample material in the input chambers of at least some of the first process arrays, and transporting the sample material from the input chambers to at least some of the primary process chambers by rotating the sample processing device about an axis of rotation located outside of the body, wherein the primary process chambers are located further from the axis of rotation than the input chambers.

These and other features and advantages of the present invention are described with respect to illustrative embodiments of the invention presented below.

DETAILED DESCRIPTION OF ILLUSTRATIVE EMBODIMENTS OF THE INVENTION

Figure 1:
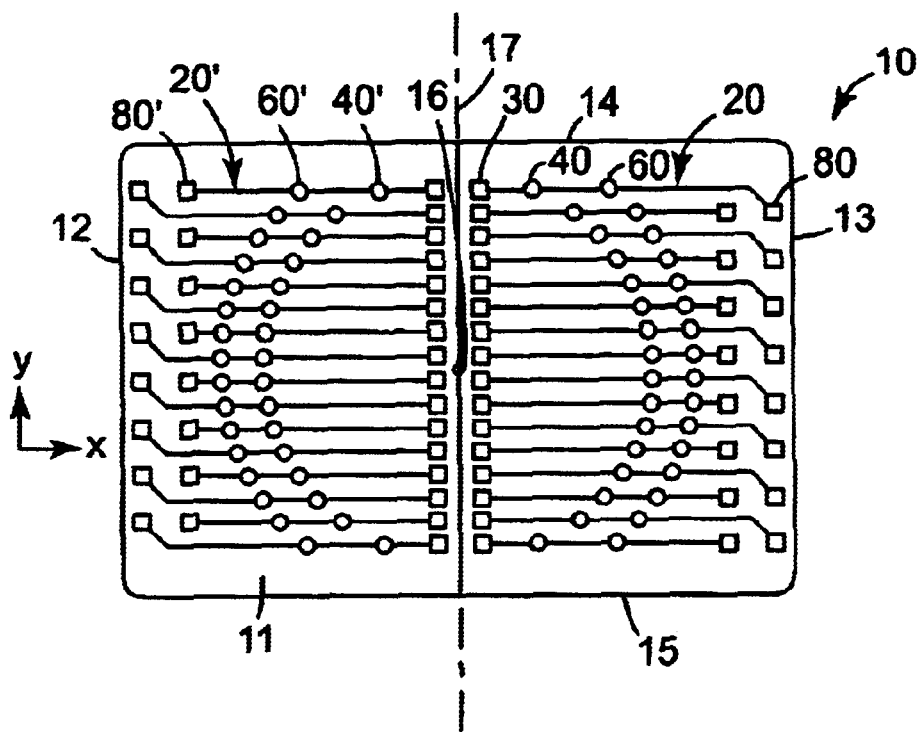
FIG. 1 is top plan view of one sample processing device according to the present invention.

The present invention provides sample processing devices, methods and systems that can be used in methods that involve thermal processing, e.g., sensitive chemical processes such as PCR amplification, ligase chain reaction (LCR), self-sustaining sequence replication, enzyme kinetic studies, homogeneous ligand binding assays, and more complex biochemical or other processes that require precise thermal control and/or rapid thermal variations.

Examples of some such processes involve chemical reactions on samples, e.g., nucleic acid amplification. For example, samples may be mixed with a polynucleotide, a polymerase (such as Taq polymerase), nucleoside triphosphates, a first primer hybridizable with the sample polynucleotide, and a second primer hybridizable with a sequence complementary to the polynucleotide. Some or all of the required reagents may be present in the device as manufactured, they may be loaded into the process chambers after manufacture of the device, they may be loaded in the process chambers just before introduction of the sample, or they may be mixed with sample before loading into the process chambers.

Although polynucleotide amplification by PCR is described in the most detail herein, the devices and methods of using them may be used for a variety of other polynucleotide amplification reactions and ligand-binding assays. The additional reactions may be thermally cycled between alternating upper and lower temperatures, such as PCR, or they may be carried out at a single temperature, e.g., nucleic acid sequence-based amplification (NASBA). The reactions can use a variety of amplification reagents and enzymes, including DNA ligase, T7 RNA polymerase and/or reverse transcriptase, etc. Polynucleotide amplification reactions that may be performed using the devices and/or methods of the invention include, but are not limited to a) target polynucleotide amplification methods such as self-sustained sequence replication (3SR) and strand-displacement amplification (SDA); b) methods based on amplification of a signal attached to the target polynucleotide, such as "branched chain" DNA amplification; c) methods based on amplification of probe DNA, such as ligase chain reaction (LCR) and QB replicase amplification (QBR); d) transcription-based methods, such as ligation activated transcription (LAT) and nucleic acid sequence-based amplification (NASBA); and e) various other amplification methods, such as repair chain reaction (RCR) and cycling probe reaction (CPR).

In addition to genetic amplification methods, other chemical or biochemical reaction applications may also be performed using the devices and/or methods of the invention. For example, temperature controlled lysis of cells may or may not be practiced in connection with the amplification processes discussed above. Furthermore, the devices and methods may be used to control and interrogate chemical reactions. By rapidly transitioning between desired temperatures, unwanted side reactions that occur at intermediate temperatures can be reduced or eliminated, potentially increasing measurement accuracy and improving product purity. Other applications other than those discussed herein may also benefit from the devices, methods and systems of the present invention.

Although construction of some illustrative embodiments of sample processing devices are described below, sample processing devices according to the present invention may be manufactured as discussed in U.S. Provisional Patent Application Ser. No. 60/214,508 filed on Jun. 28, 2000 and titled THERMAL PROCESSING DEVICES AND METHODS and U.S. Provisional Patent Application Ser. No. 60/214,642 filed on Jun. 28, 2000 and titled SAMPLE PROCESSING DEVICES, SYSTEMS AND METHODS. Other potential device constructions may be found in, e.g., U.S. patent application Ser. No. 09/710,184 filed on Nov. 10, 2000 and titled CENTRIFUGAL FILLING OF SAMPLE PROCESSING DEVICES; U.S. patent application Ser. No. 60/237,151 filed on Oct. 2, 2000 and titled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METHODS; and U.S. Provisional Patent Application Ser. No. 60/284,637 filed on Apr. 18, 2001 and titled ENHANCED SAMPLE PROCESSING DEVICES, SYSTEMS AND METHODS.

Although terms such as "top" and "bottom" may be used in connection with the present invention, it should be understood that those terms are used in their relative sense only. In use, elements described as "top" or "bottom" may be found in any orientation.

One illustrative sample processing device manufactured according to the principles of the present invention is depicted in FIG. 1. It will be understood that the exact number of process arrays, process chambers, etc. on the depicted sample processing device 10 is exemplary only, and that the actual number of such features provided in connection with a sample processing device manufactured according to the present invention may be greater than or less than those found in the depicted device 10.

The features in the illustrative device 10 are described in the form of chambers, although the process chambers in devices of the present invention may be provided in the form of capillaries, passageways, channels, grooves, or any other suitably defined volume.

The sample processing device 10 includes a rectangular body to improve compatibility of the sample processing device 10 with equipment designed for use with more conventional microtiter plates (which are typically rectangular in shape). Slight deviations from a true rectangle in the shape of the body 11 are considered to fall within the scope of the present invention, although the body 11 should have four identifiable corners at the junctions of four identifiable sides and two major surfaces. The sides need not necessarily form straight lines, provided the sample processing devices fit within the rectangular form factor of conventional microtiter plates. The body 11 includes two sides 12 and 13 at opposing ends of the device 10 and two sides 14 and 15 extending between the two ends. The body 11 of the device 10 also includes a center of rotation 16 about which the device 10 is designed to be rotated as discussed in more detail below.

FIG. 1 is a top plan view of the device 10 illustrating one of the two major surfaces of the body 11, which is preferably in the form of a card-shaped device. As such, the body 11 preferably has a thickness that is substantially less than the length or width of the major surfaces of the body 10. By providing the sample processing device 10 with a limited thickness, speed in thermal processing may be facilitated as discussed below.

The sample processing device 10 includes two halves, each with essentially the same features. For simplicity, the discussion below will focus mainly on the features found on the right side of the sample processing device 10 as seen in FIG. 1. It should, however, be understood that the description is equally applicable to the corresponding features found on the left side of the device 10 (which are referenced with prime numbers, e.g., 20').

The sample processing device 10 includes a number of groups of interconnected chambers and other features that will be referred to herein as process arrays 20. One exemplary process array 20 is depicted in an enlarged top plan view in FIG. 2.

Each of the process arrays 20 of the sample processing device 10 includes a number of common components including an input chamber 30, primary process chamber 40, secondary process chamber 60 and an output chamber 80. It should be understood that process arrays in sample processing devices according to the present invention may include only some of these components. For example, the process arrays may include only input chambers, primary process chambers and output chambers in one simpler form.

Further, the process arrays may include additional optional components other than those depicted. Such components may include (but are not limited to) filtering chambers, additional valves associated with the filtering chambers, wash ports/chambers, vents, etc.

In sample processing devices of the present invention, it will typically be preferred that the input chamber 30 be located closer to the center 16 of the device 10 than any process chambers and the output chamber within the same process array 20 as the input chamber 30. By locating the input chamber 30 closer to the center 16, rotation of the device 10 about the center 16 causes materials located in the input chamber 30 to move towards the other chambers of the process array 20.

Figure 2:
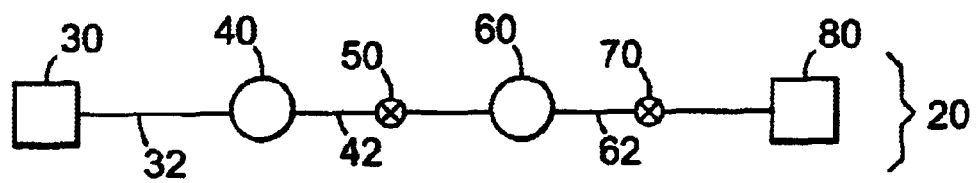
FIG. 2 is an enlarged view of one process array on the sample processing device of FIG. 1.

The process array 20 depicted in FIG. 2 includes additional optional components such as valve 50 located between the primary process chamber 40 and the secondary process chamber 60, and valve 70 located between the secondary process chamber 60 and the output chamber 80. The various components of the process arrays 20 are connected by channels such that sample materials, reagents, filtering materials, etc. can be transported between the various chambers in the process array 20.

For example, the input chamber 30 is connected to the primary process chamber 40 by channel 32. The primary process chamber 40 is connected to the secondary process chamber 60 through channel 42, with optional valve 50 being located between the primary process chamber 40 and the secondary process chamber 60 to control the flow of materials between the two process chambers 40 and 60. In the process array 20, the secondary process chamber 60 is connected to the output chamber 80 through channel 62. An optional valve 70 is located between the secondary process chamber 60 and the output chamber 80 to control the flow of materials between the two chambers 60 and 80.

Referring again to FIG. 1, and more specifically to the right side of the sample processing device 10 as depicted in FIG. 1, the primary process chambers 40 in each of the process arrays 20 are arranged in a circular arc on the surface of the sample processing device 10. In the depicted embodiment, the center 16 of the circular arc along which the primary process chambers 40 are arranged is coincident with the center of the rectangularly-shaped body 11.

It may further be preferred that the left and right halves of the sample processing device 10 be at least partially symmetrical about an axis of symmetry 17 extending through the center 16 of the circular arc. Such a symmetrical device 10 would preferably include, on the left side, process arrays 20' with primary process chambers 40' arranged along a circular arc that has a center coincident with the center 16 of the circular arc along which the primary process chambers 40 of process arrays 20 on the right side of the axis 17. As a result, the circular arcs formed by both sets of primary process chambers 40 and 40' define one primary process chamber circle with a center located at point 16.

Similarly, the secondary process chambers 60 and 60' on both sides of the axis of symmetry 17 may also be arranged in circular arcs with their centers coincident at the center 16. If so arranged, the secondary process chambers 60 and 60' would define a secondary process chamber circle with a center also located at center 16.

Either or both of the input chambers 30 and the output chambers 80 of the process arrays 20 and 20' are arranged on the sample processing device 10 in a rectilinear grid array. In the depicted sample processing device 10, both sets of chambers, i.e., the input chambers 30 and the output chambers 80 are arranged in rectilinear grid arrays. In rectilinear grid arrays, the spacing between the input chambers 30 or the output chambers in the different process arrays 20 is regular in both the x and y directions (see the coordinate system in FIG. 1). This arrangement is preferably compatible with conventional robotic pipetting systems. With the input chambers 30, it allows for automated delivery of sample materials, filtering materials, reagents, etc. For example, it may be possible to deliver materials to the input chambers 30 using a standard 8-tip robotic pipetting tool with 9 millimeter spacing. In the case of the output chambers 80, the rectilinear grid array may allow for automated detection of processing results, automated retrieval of completed sample materials, etc.

Alternatively, it may be possible to deliver and/or remove materials from the process chambers 40/40' and 60/60' arranged in circular arcs with appropriately designed tooling that would provide equipment arranged in complementary circular arcs. As such, automated delivery and/or removal of materials from the chambers arranged in circular arcs could also be performed.

It should be noted that the symmetry exhibited by the primary and secondary process chambers 40/40' and 60/60' may or may not be exhibited by the input and output chambers. For example, the input chambers 30 and 30' on opposite sides of the axis of symmetry 17 are symmetrical about that axis. In contrast, the output chambers 80 and 80' on opposite sides of the axis of symmetry 17 are not symmetrical about that axis. Regardless of that lack of symmetry, however, the output chambers 80 and 80' are arranged in rectilinear grid arrays that are compatible with one another, i.e., the rectilinear grid array of the output chambers 80 on the right side of the device 10 is consistent with the rectilinear grid array defined by the output chambers 80' on the left side of the device 10. In other words, if the pattern defined by the output chambers 80 on the right side of the device 10 were repeated over the entire device 10, the locations of the output chambers 80' on the left side of the device would be consistent with that rectilinear grid array.

The actual construction of the sample processing devices of the present invention may vary. Many different constructions are discussed in the related applications identified above. One exemplary construction for the sample processing device 10 will now be described, but it should be understood that this description is not to limit the present invention, unless explicitly recited in the claims. The construction of one process array 20 in the device 10 is depicted in cross-section in FIG. 3, where the sample processing device 10 includes a core 90 in which a variety of structures are formed A first cover layer 100 is attached to a first major side 92 of the core 90 and a second cover layer 102 is attached to a second major side 94 of the core 90.

The core 90 may preferably be polymeric, but may alternatively be made of other materials such as glass, silicon, quartz, ceramics, etc. Furthermore, although the core 90 is depicted as a homogenous, one-piece integral body, it may alternatively be provided as a non-homogenous body of, e.g., layers of the same or different materials.

The first cover layer 100 may be a single, homogeneous layer as depicted, or it may include multiple sub-layers. In some embodiments that include multiple sub-layers, it may be preferred that the first cover layer 100 include a reflective sub-layer (e.g., metallic, polymeric, etc.). The second cover layer 102 may include, e.g., an adhesive and a substrate, both of which may be optically clear or otherwise transmissive to electromagnetic energy of selected wavelengths.

For those devices 10 in which the core 90 and/or cover layers 100 and 102 will be in direct contact with the sample materials, it may be preferred that the material or materials used for the components be non-reactive with the sample materials. Examples of some suitable polymeric materials that could be used for the substrate in many different bioanalytical applications may include, but are not limited to, polycarbonate, polypropylene (e.g., isotactic polypropylene), polyethylene, polyester, etc.

The first and second cover layers 100 and 102 may be attached to the core 90 by any suitable technique or techniques. The first and second cover layers 100 and 102 may be attached to the core 90 by the same or different techniques, including adhesives, welding (ultrasonic, chemical, etc.), heat sealing, etc. Suitable techniques for attaching the cover layers 100 and 102 to the core 90 may need to exhibit sufficient strength to resist the expansive forces that may develop within the process chambers as, e.g., the constituents located therein are rapidly heated during thermal processing. The robustness of the bonds between the components may be particularly important if the sample processing device 10 is to be used for thermal cycling processes, e.g., PCR amplification. The repetitive heating and cooling involved in such thermal cycling may pose more severe demands on the bond between the components of the device 10. Another potential issue addressed by a more robust bond between the components is any difference in the coefficients of thermal expansion of the different materials used to manufacture the components.

Among the features of the process array 20 that are formed in the core 90 are the input chamber 30 that, in the illustrated embodiment, is formed only partially through the core 20, although it could alternatively be formed completely through both major sides 92 and 94 of the core 90. The input chamber 30 is in fluid communication with a primary process chamber 40 through a channel 42 that is also formed in the core 90. The primary process chamber 40 is formed as a void extending through both major sides 92 and 94 of the core 90.

The secondary process chamber 60 of process array 20 is also formed in the core 90 as a void through both major sides 92 and 94. The secondary process chamber 60 is in fluid communication with the primary process chamber 40 only when valve 50, located between the primary and secondary process chambers 40 and 60, is in the open condition. A portion of the channel 42 formed in the first major side 92 of the core 90 connects the primary process chamber 40 to the valve 50 and another portion of the channel 42 (formed in the second major side 94 of the core 90) connects the valve 50 to the secondary process chamber 60.

The valve 50 is useful to control the movement of materials between the primary process chamber 40 and the secondary process chamber 60. The depicted valve 50 is provided in the form of an impermeable membrane 52 located within via 54 connecting the first portion of the channel 42 with the second portion of the channel 42. The membrane 52 can be pierced or ablated when desired to place it in the open state. The valve 50 may, however, be provided in a number of forms, e.g., a thermal plug (e.g., waxes, etc.), shape-memory materials, expandable materials (e.g., foams, etc.) or other structures/materials that can be opened when desired. Alternatively, the function of the valve 50 may be provided by varying the rotational speed of the disc to overcome the resistance of materials to move through the channel 42 and/or via 54.

The process array 20 also includes an output chamber 80 that, like the input chamber 30, is formed only partially through the core 90 of the sample processing device 10. The output chamber 80 is in communication with the secondary process chamber 60 only when valve 70, located between the secondary process chamber 60 and the output chamber 80, is in the open condition. A portion of the channel 62 (formed in the first major side 92 of the core 90) connects the secondary process chamber 60 to the valve 70 and another portion of the channel 62 (formed in the second major side 94 of the core 90) connects the valve 70 to the output chamber 80.

The valve 70 is provided in the form of an impermeable membrane 72 located within a via 74, similar to valve 50 located between the primary and secondary process chambers 40 and 60. It will, however, be understood that the valve 70 may take any desired form that provides the function of controlling the movement of materials from the secondary process chamber 60 to the output chamber 80.

In addition to opening valves during distribution of material through the process arrays 20, it may be desirable seal or isolate portions of the process array after, e.g., the primary process chamber 40 is loaded with sample material. One isolation technique may involve closing the channel 32 leading from the input chamber 30 to the primary process chamber 40 by compressing the cover layer 100 against the core 90. Sealing of the channel 32 may be accomplished mechanically, i.e., by simply crushing the channel 32, or it may be accompanied by the application of heat to enhance adhesion of the cover layer 100 to the core 90. Alternatively, sufficient isolation may be achieved by continuously rotating the device 10 during processing, such that the sample materials are retained in the process chambers by centrifugal forces.

Figure 3:
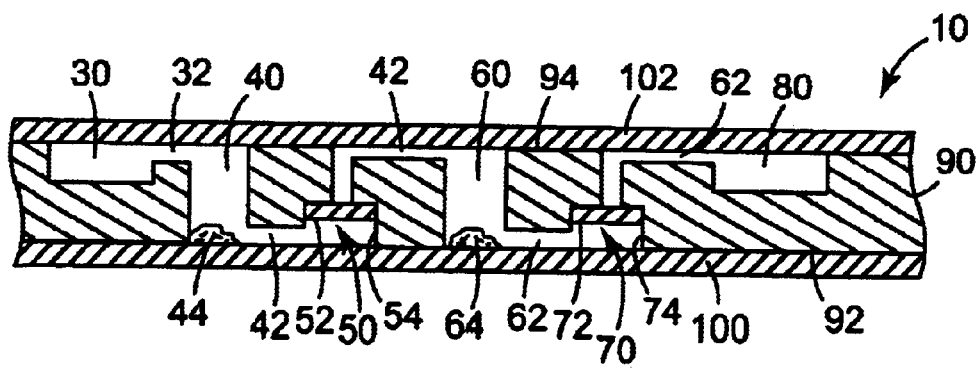
FIG. 3 is an enlarged cross-sectional view of one process array on the sample processing device of FIG. 1.

Also depicted in FIG. 3 is a reagent 44 located within the primary process chamber 40 and a reagent 64 located within the secondary process chamber 60. The reagents 44 and 64 may preferably be fixed to a surface within the respective process chambers. The reagents 44 and 64 are optional, i.e., some sample processing devices 10 may or may not include any reagents loaded in the primary and secondary process chambers 40 and 60. In another variation, some of the process chambers may include one or more reagents while others do not. In yet another variation, different process chambers may contain different reagents.

The arrangement of the process arrays on the sample processing device 10 allows for transport of materials through the process arrays by rotating the device 10 about an axis of rotation extending through center 16 of the device 10 such that the sample materials are moved outwardly due to centrifugal forces generated during rotation. Before the device 10 is rotated, the sample materials can be introduced into the input chambers 30 and 30' for delivery to the process chambers. The process arrays 20 and 20' may include ports through which air can escape and/or other features to assist in distribution of the sample materials to the process chambers. Alternatively, sample materials could be loaded into the process arrays under the assistance of vacuum or pressure.

It may, however, be preferred that the process arrays 20 and 20' of the sample processing device 10 be "unvented". As used in connection with the present invention, an "unvented process array" is a process array in which openings leading into the volume of the process array (including process chambers, channels, output chambers, etc.) are located in the input chamber. In other words, to reach the primary process chamber 40 within an unvented process array, sample materials must be delivered to the input chamber 30. Any air or other fluid located within the unvented process array before loading with sample material must also escape from the process array 20 through the input chamber 30. In contrast, a vented process array would include at least one opening outside of the input chamber. That opening would allow for the escape of any air or other fluid located within the process array before loading during distribution of the sample material through the process array.

In another alternative, the input chamber 30 in an unvented process array 20 may itself be sealed after it is loaded with sample materials. In such an unvented process array, sample materials can still be transferred out to the process chambers during rotation as the sample material, reagents, etc. in the input chamber 30 are exchanged with any gases (e.g., air, etc.) located in the process chambers.

Moving sample material within sample processing devices 10 that include unvented process arrays may be facilitated by alternately accelerating and decelerating the device 10 during rotation, essentially burping the sample materials through the process arrays 20. The rotating may be performed using at least two acceleration/deceleration cycles, i.e., an initial acceleration, followed by deceleration, second round of acceleration, and second round of deceleration.

It may further be helpful if the acceleration and/or deceleration are rapid. The rotation may also preferably only be in one direction, i.e., it may not be necessary to reverse the direction of rotation during the distribution process. Such a distribution process allows sample materials to displace the air in those portions of the process array 20 that are located farther from the center of rotation of the device 10 than the opening into the process array. One advantage of an unvented process array, i.e., a process array including at least some channels and process chambers outside (radially) of any vents, is that leakage from those vents is prevented.

The actual acceleration and deceleration rates may vary based on a variety of factors such as temperature, size of the device, distance of the sample material from the axis of rotation, materials used to manufacture the devices, properties of the sample materials (e.g., viscosity), etc. One example of a useful acceleration/deceleration process may include an initial acceleration to about 4000 revolutions per minute (rpm), followed by deceleration to about 1000 rpm over a period of about 1 second, with oscillations in rotational speed of the device between 1000 rpm and 4000 rpm at 1 second intervals until the sample materials have traveled the desired distance.

It may be preferred that at least a portion of the materials defining the volume of the process chambers in the process arrays 20 be transmissive to electromagnetic energy of selected wavelengths. The selected wavelengths may be determined by a variety of factors, for example, electromagnetic energy designed to heat and/or interrogate a sample in the process chambers, electromagnetic energy emitted by the sample (e.g., fluorescence), etc. In another alternative, the sample processing devices may be manufactured of materials or include additional materials that shield the process chambers from electromagnetic energy in the ultraviolet spectrum.

In the sample processing device 10, it may be preferred that at least the output chambers 80 be transmissive to electromagnetic energy of selected wavelengths. By providing a transmissive output chamber 80, a sample in the output chamber can be interrogated by electromagnetic energy of selected wavelengths (if desired) and/or electromagnetic energy of the selected wavelengths emanating from the sample can be transmitted out of the output chamber 80 where it can be detected by suitable techniques and equipment. For example, electromagnetic energy may be emitted spontaneously or in response to external excitation. A transmissive output chamber 80 may also be monitored using other detection techniques, such as color changes or other indicators of activity or changes within the output chambers.

Figure 4:
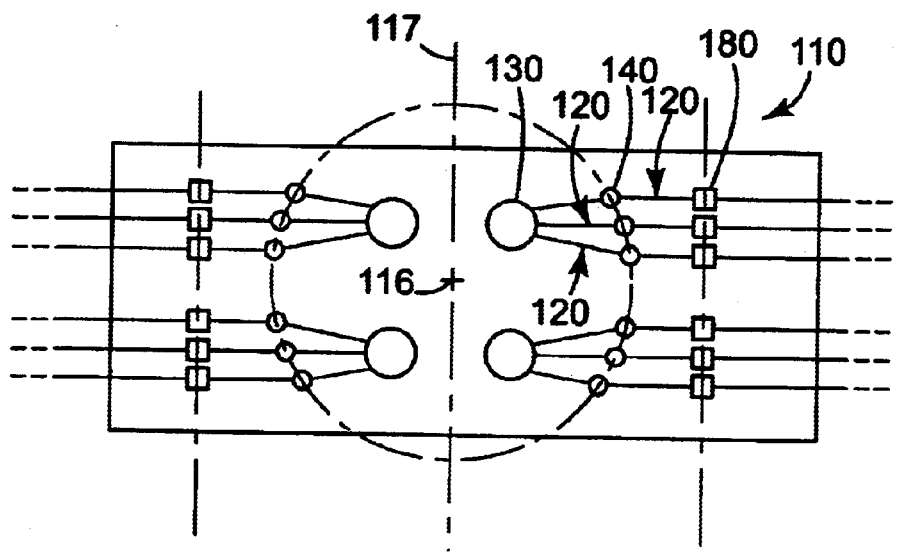
FIG. 4 depicts an alternative sample processing device according to the present invention.

FIG. 4 depicts an alternative embodiment of a sample processing device 110 according to the present invention. The sample processing device 110 includes a number of process arrays 120 that are similar in many respects to the process arrays 20 described above in connection with sample processing device 10. For example, each of the process arrays 120 includes an input chamber 130, primary process chamber 140 and an output chamber 180. Unlike the sample processing device 10 depicted in FIGS. 1–3, the process arrays 120 on the device 110 do not include a secondary process chamber.

The process arrays 120 on the sample processing device 110 also share common input chambers 130 such that each input chamber 130 is connected with two or more primary process chambers 140. As depicted in FIG. 4, three process arrays 120 are connected to each of the input chambers 130. In some instances, all of the process arrays 120 on one side of a symmetrical sample processing device may be connected to a single, common input chamber.

It is preferred that the input chambers 130 are arranged in a rectilinear grid array that may preferably also be symmetrical about an axis of symmetry 117 extending through center 116 on the sample processing device. The primary process chambers 140 are also arranged along circular arcs that also have their center coincident with the center 116. The circular arcs formed by the primary process chambers 140 also preferably define a primary process chamber circle with a center that is also coincident with center 116. Further, it may also be preferred that the output chambers 180 of the process arrays 120 also be arranged in a rectangular grid array.

Figure 5:
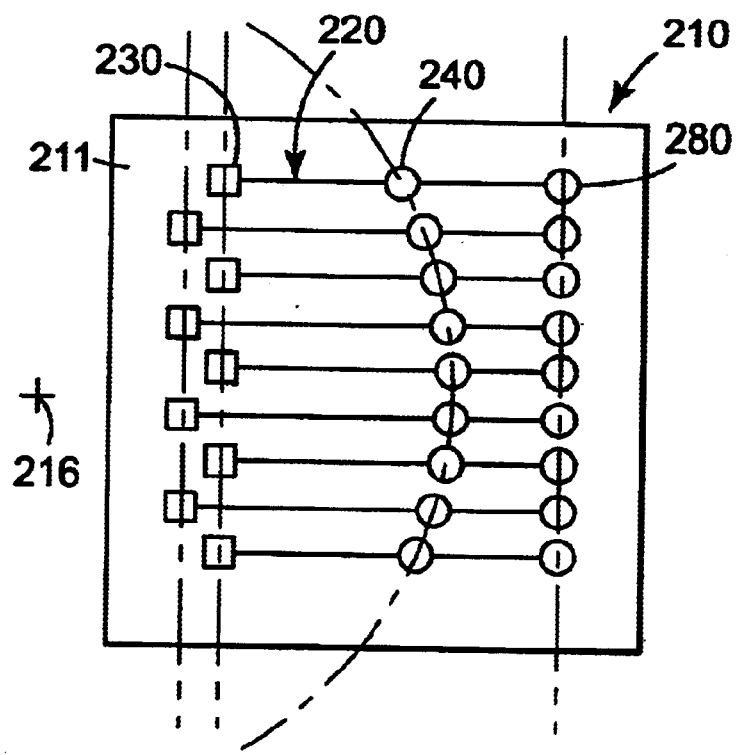
FIG. 5 depicts another alternative sample processing device according to the present invention.

FIG. 5 depicts another alternative embodiment of a sample processing device 210 according to the present invention. The body 211 of the device 210 is in the shape of a square. The device 210 includes process arrays 220 that extend between opposing sides of the device 210 such that the input chambers 230 are located proximate one side and the output chambers 280 are located proximate the opposing side of the sample processing device 210.

The input chambers 230 and output chambers 280 are, however, preferably arranged in rectilinear grid arrays, while the primary process chambers 240 are arranged in a circular arc that preferably has a center 216. As depicted in FIG. 5, the center of the circular arc is not necessarily located within the bounds of the body 211 of the sample processing device 210.

Figure 5A:
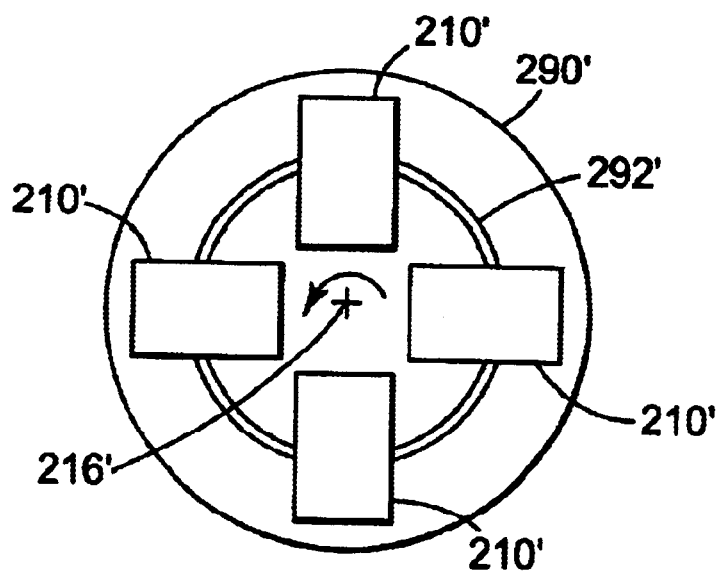
FIG. 5A depicts one arrangement of sample processing devices according to the present invention on a base plate.

One system that may be used to process sample processing devices such as those depicted in FIG. 5 is depicted in FIG. 5A. The system includes a number of sample processing devices 210' located on a base plate 290' that can be rotated about a central axis of rotation 216' that is located outside of the bodies of each of the sample processing devices 210'. The base plate 290' may preferably include a thermal structure 292' in the form of a ring on the base plate 290'. Such structures are described in more detail below with respect to FIGS. 6A, 6B, and 7–9. Alternatively, the base plate 290' may be rotated beneath a source of electromagnetic energy directed at the process chambers located within circular arcs as discussed above. Advantages of the system depicted in FIG. 5A include the ability to process multiple sample processing devices 210' at the same time, thereby increasing throughput.

Figure 6A:
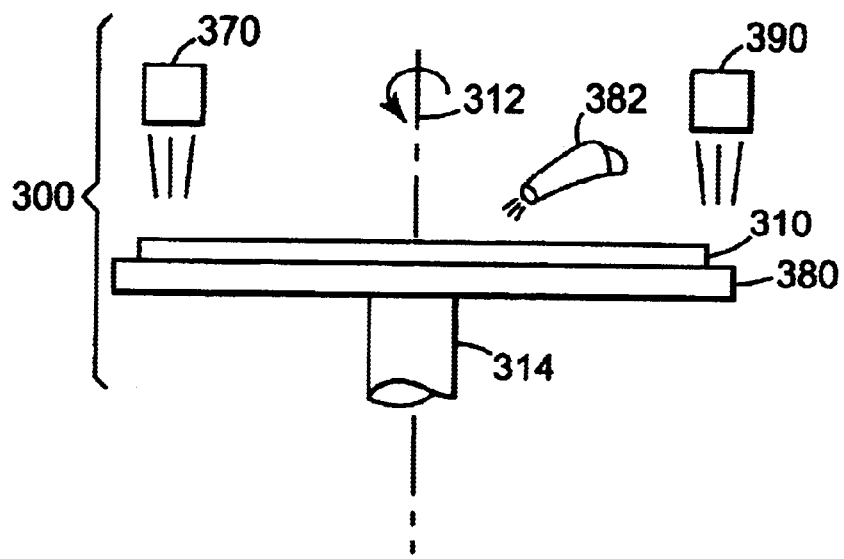
FIG. 6A is a side elevational view of one thermal processing system according to the present invention.
Figure 6B:
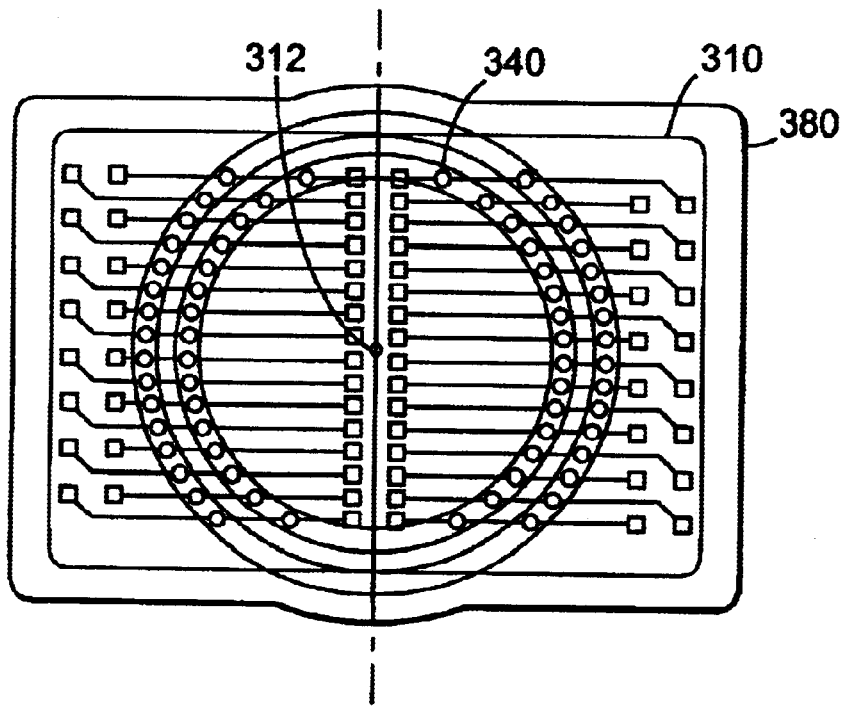
FIG. 6B is a top plan view of the system of FIG. 6A.

One illustrative system for accomplishing a thermal cycling process using a sample processing device 310 according to the present invention is schematically depicted in FIGS. 6A & 6B. The system 300 includes a sample processing device 310 located on a spindle 314 that rotates the device about an axis 312. The device 310 includes process arrays into which a sample material is distributed as discussed above.

After distribution of the sample material into the process arrays on the sample processing device 310, individual process chambers 340 can be selectively heated by suitable electromagnetic energy supplied by an electromagnetic energy source 370 that heats the materials in the process chambers 340. Because the process chambers 340 on sample processing device 310 are arranged in circular arcs and the device 310 is rotated about axis 312 which extends through the centers of the circular arcs, rotation of the sample processing device 310 as depicted brings the process chambers 340 into alignment with the electromagnetic energy source 370 for heating.

The electromagnetic energy source 370 is preferably remote from the sample processing device 310, i.e., it is not located on the device 310. Examples of some suitable electromagnetic energy sources may include, but are not limited to, lasers, broadband electromagnetic energy sources (e.g., white light), etc. The electromagnetic energy source 370 may be provided continuously or intermittently based on a variety of factors, e.g., the desired temperature of the sample materials, the rate at which thermal energy is removed from each process chamber, the desired rate of temperature change, whether the process chambers include a reflective component, etc.

As the sample processing device 310 rotates, it is preferred that the airflow over the surface of the device 310 assists in cooling the sample materials in the process chambers 340 to a selected base temperature from the upper target temperature to which the sample materials are heated by the electromagnetic energy from the source 370. In some systems, one or both surfaces of the device 310 may be exposed to the atmosphere to also assist in cooling. The system 300 as depicted in FIGS. 6A & 6B, however, includes an optional base plate 380 that may be held at a lower temperature. By holding one surface of the sample processing device 310 in contact with the base plate 380, it may be possible to assist in cooling the sample materials in the process chambers 340 between heating cycles as the device 310 rotates during processing. If a base plate 380 is used to assist in thermal control, it may be helpful to use a sample processing device 310 incorporating a metallic layer proximate the base plate 380 to improve thermal conductivity between the base plate and the device 310.

In other systems, it may be desirable to promote both heating and cooling of the process chambers through the base plate 380. For example, heating and cooling may be facilitated by incorporating thermoelectric modules (e.g., Peltier elements, resistive heaters, etc.) in the base plate 380 underneath each of the process chambers 340. A thermoelectric module may be provided in the form of a ring located beneath the process chambers 340 or a number of individual thermoelectric modules may be used in connection with base plate 380. The heating of process chambers 340 using base plate 380 may be performed in connection with heating using electromagnetic energy source 370 to provide even faster heating and/or more uniform temperature distribution of the process chambers 340. Thus, the control over sample material temperature may be accomplished by simultaneously delivering electromagnetic energy to the process chambers 340 and controlling the temperature of thermoelectric modules above which the process chambers 340 are located.

The system 300 depicted in FIGS. 6A & 6B also includes an optional additional temperature control mechanism in the form of a fluid source 382, e.g., pressurized air or any other suitable fluid, that can be directed at the surface of the sample processing device 310. The fluid used can be either heated or cooled to a desired temperature. Where it is desired to cycle the sample materials between upper and lower temperatures, the fluid may be provided at the lower temperature. Although depicted as being directed at only one surface of the sample processing device 310, it will be understood that the fluid may be directed at both surfaces of the device 310 if desired.

The system 300 may also include various other components such as a detection system 390 provided to detect the results of processing of the sample materials in the process chambers 340. For example, the detection system and method may involve active interrogation of the process chambers 340 to detect fluorescent reaction products in the chambers as the sample processing device 310 rotates. The detection may be qualitative or quantitative. Other detection systems may be provided to monitor, e.g., the temperatures or other properties of the materials in the process chambers 340.

As the thermal cycling method is performed, the temperature within the process chambers 340 may be monitored to control the application of energy into the process chambers 340. Among the variables that may be manipulated to control the sample material temperatures in the sample processing device 310 include the intensity of the laser or other light source, the rotational speed of the device 310 (which can affect the cooling rate and the dwell time of each of the process chambers in the laser or other light source), the temperature of the base plate 380 (or any components such as thermoelectric modules located in the base plate 380), and the temperature and pressure of the fluid source 382.

If the sample processing device 310 includes unvented process arrays, another advantage of rotating the device 310 during heating is that, as the temperature of the sample materials rises and vapor is formed, it must travel upstream, i.e., towards the axis of rotation of the device 310 (where the only opening into each unvented process array is located). Once outside of the process chamber 340, however, the thermal energy dissipates, causing the vapors to condense. The condensed sample materials are then returned to the process chambers 340 due to the centrifugal forces provided by the rotation. The end result is that the sample materials are, for the most retained in the process chambers 340, even during rapid heating that may cause some vaporization.

Figure 7:
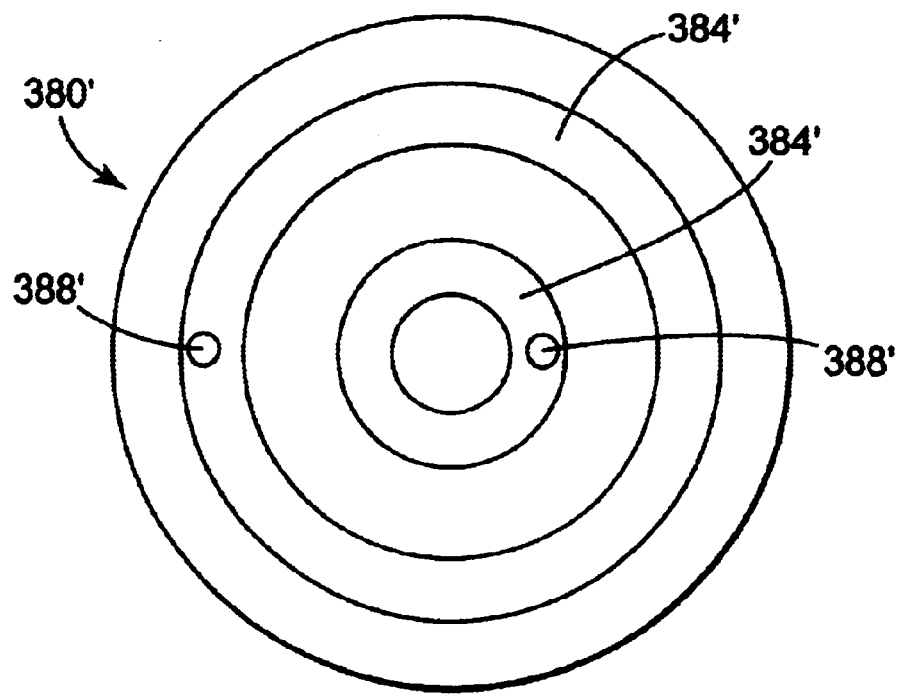
FIG. 7 is a plan view of an alternative base plate for a thermal processing system according to the present invention.
Figure 8:
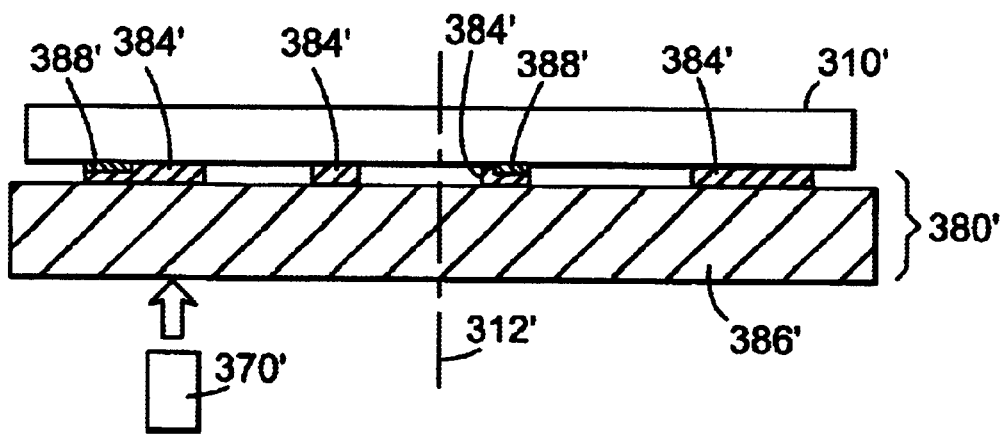
FIG. 8 is a cross-sectional view of the base plate of FIG. 7 with a sample processing device 310' located thereon.

FIGS. 7 and 8 depict an alternative base plate 380' design that includes at least one thermal structure 384' constructed of a material that absorbs electromagnetic energy. The thermal structures 384' are located beneath at least some of the process chambers of sample processing device 310' (see FIG. 8) such that heating or cooling of the thermal structures 384' causes corresponding temperature variations in the process chambers located above the top surface of the thermal structure 384' as thermal energy is conducted into and/or out of the thermal structures 384'.

The thermal structures 384' may preferably be heated by an electromagnetic energy source 370' that, in the depicted embodiment, is located on the opposite side of the thermal structures 384' from the sample processing device 310' and directs electromagnetic energy at the bottom surface of the thermal structures 384'. Thermal energy is transferred between the sample processing device 310' and the thermal structures 384' primarily by conduction. Although base plate 380' is depicted with two thermal structures 384', it will be understood that the base plate 380' could include any number of thermal structures 384' necessary to transfer thermal energy to or from the selected process chambers in a sample processing device 310'. Further, it may be preferred that, where more than one thermal structure 384' is provided, the thermal structures 384' be independent of each other such that thermal energy is not transferred between the independent thermal structures 384'.

The electromagnetic energy source 370' may be in a form that provides electromagnetic energy to only one thermal structure 384' at a time, or it may be capable of heating two or more thermal structures 384' simultaneously. If heating of different thermal structures 384' at different times is desired, it may be desirable to provide a separate electromagnetic energy source 370' dedicated to each thermal structure 384', to move a single energy source 370' such that it is positioned facing the thermal structure 384' to be heated, to provide a shuttering system that provides electromagnetic energy to the necessary thermal structure 384' at the selected time, etc.

The thermal structures 384' may be constructed of a variety of materials, provided the materials possess sufficient thermal conductivity and absorb electromagnetic energy at sufficient rates. In addition, it may also be desirable that the material or materials used for the thermal structures 384' have sufficient heat capacity to provide a heat capacitance effect. Examples include, but are not limited to: aluminum, copper, gold, etc. If the thermal structures 384' are constructed of materials that do not, themselves, absorb electromagnetic energy at a sufficient rate, it may be preferred that the thermal structures 384' include a material that improves energy absorption. For example, the thermal structures 384' may be coated with an electromagnetic energy absorptive material such as carbon black, polypyrrole, inks, etc.

One potential advantage of using thermal structures 384' in conjunction with the electromagnetic source 370' is that compatibility between the electromagnetic energy source and any reagents or other materials located within the process chambers of the sample processing device 310' may be improved. The thermal structures 384' may preferably be opaque to the electromagnetic energy produced by source 370'. As a result, materials within the process chambers may be substantially shielded from direct exposure to the electromagnetic energy that could, in some instances, be detrimental to the desired reactions.

Although the thermal structures 384' are depicted as being located on the top surface of a sub-plate 386', it will be understood that any suitable design that incorporates thermal structures 384' could be used. For example, the thermal structures 384' could be embedded in the sub-plate 386' or no sub-plate 386' could be provided (with the thermal structures 384' interconnected by, e.g., a series of radial struts or other structures). Where a sub-plate 386' is used, however, it may preferably be transmissive to the electromagnetic energy, such that the electromagnetic energy is able to reach the thermal structures 384' to provide the desired thermal heating effect.

Alternatively, the sub-plate 386' may include openings that expose selected portions of the thermal structures 384' to the electromagnetic energy provided by electromagnetic energy source 370'. Where the sub-plate 386' includes openings to expose the bottom surface of the thermal structures 384', the materials of the sub-plate 386' may be opaque to the electromagnetic radiation from the electromagnetic source 370'.

It may further be desirable that the thermal structures 384' be relatively thermally isolated from the sub-plate 386' such that only limited amounts (if any) of the thermal energy in the thermal structures 384' is transferred to the sub-plate 386'. That thermal isolation may be achieved, for example, by manufacturing the sub-plate 386' of materials that absorb only limited amounts of thermal energy, e g. polymers, etc.

The base plate 380' may also optionally include sensors to detect the temperature of the rings 384'. FIGS. 7 and 8 depict two sensors 388' located within the thermal structures 384' and information from the sensors 388' may be used to control the amount of energy provided by the electromagnetic energy source 370' or to control the rate and/or duration of rotation of the base plate 380' as a part of any system control over both heating and cooling of the rings 384'. Alternatively, the ring temperature or the temperature within the process chambers on sample processing device 310' may be monitored remotely by, e.g., infrared emissions, etc.

Although the base plate 380' of FIGS. 7 and 8 includes thermal structures 384' in the form of substantially continuous circular rings, the thermal structures 384' may alternatively be provided as a series of discontinuous shapes, e.g., circles, squares, located beneath process chambers on the sample processing device 310' that are to be heated by conduction. One advantage, however, of a continuous ring thermal structure is that temperature of each thermal structure 384' may equilibrate during heating, thereby potentially improving chamber-to-chamber temperature uniformity for all process chambers located above the continuous thermal structure.

Methods of using the base plate 380' will, in most aspects, be similar to the use of system 300 described above, with the addition of the electromagnetic source 370' directed at the thermal structures 384' in the base plate 380'. The energy provided by the electromagnetic energy source 370' may be controlled to obtain the desired temperatures in the process chambers (by, e.g., varying the power output of the source 370', providing a shutter system, etc.).

The heating of process chambers using thermal structures 384' in base plate 380' may be performed in connection with heating using an electromagnetic energy source located above the sample processing device 310' to provide even faster heating and/or more uniform temperature distribution of the process chambers in the device 310'. In such a system and method, electromagnetic radiation may be delivered directly to the process chambers (referring to the system and method depicted in FIGS. 6A & 6B) while the process chambers are simultaneously being heated by thermal energy conduction from below using thermal structures 384'. In another alternative, the process chambers in the sample processing device 310' may be heated using only the thermal structures 384', i.e., without the need to direct any electromagnetic energy directly into the process chambers using, e.g., an electromagnetic energy source 370 located above the sample processing device 310'.

Figure 9:
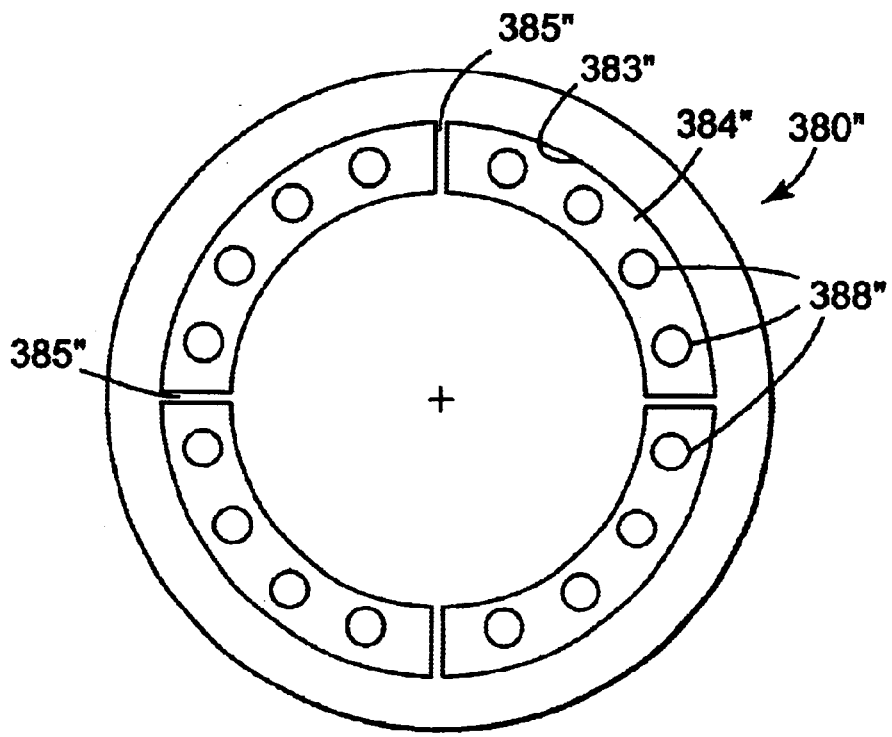
FIG. 9 is a plan view of an alternative base plate for a thermal processing system according to the present invention.

In yet another variation depicted in FIG. 9, the bottom of a base plate 380" is depicted. A series of openings 383" are provided in the bottom of the base plate 380" with the openings 383" being separated by struts 385". The bottom surface of a thermal structure 384" is exposed within the openings 383" such that electromagnetic energy directed at the thermal structure 384" can be absorbed and converted to thermal energy as described above.

Also seen in FIG. 9 are thermoelectric modules 388" either attached to or embedded within the thermal structure 384". The thermoelectric modules 388" may be provided in the form of, e.g., Peltier elements, resistive heaters, etc. Although a number of thermoelectric modules 388" are depicted, a single thermoelectric module may alternatively be provided.

With the base plate 380", control over the temperature of the thermal structures 384' may be effected by using the thermoelectric modules 388" alone or in combination with electromagnetic energy directed at the bottom surface of the thermal structures 384'. Where the temperature of the thermal structure 384" is to be controlled by the thermoelectric modules 388" alone (i.e., where the thermal structure 384" is not to be heated by converting electromagnetic energy directed at the bottom surface of the thermal structure 384" to thermal energy), the materials selected for manufacturing the thermal structure 384" may be chosen based on their thermal conductivity, with no consideration given for the ability of the materials to absorb electromagnetic energy. Suitable materials may include but are not limited to, e.g., metals (such as, e.g., aluminum, gold, copper, etc.).

By combining the thermoelectric modules 388" with the thermal structure 384" advantages may be obtained in the form of improved temperature uniformity as the thermal structure 384" serves as a sink to equilibrate variations in the operating characteristics of the individual thermoelectric modules 388".

The thermoelectric modules 388" provide another option in controlling the temperature of sample materials in the process chambers of device located above the thermal structure 384". The thermoelectric modules 388" may be used in addition to the delivery of electromagnetic energy directly into the process chambers and the delivery of electromagnetic energy to the thermal structure 384" to provide three heat sources. Alternatively, the thermoelectric modules 388" may be used alone to heat the process chambers on a device located above the base plate 380" or they may be used in connection with the delivery of electromagnetic energy directly into the process chambers of the sample processing device (in the absence of electromagnetic energy directed at the bottom surface of the thermal structure 384". The net result is that in a system having the ability to provide electromagnetic energy directly to the process chambers, thermal structures that can convert impinging electromagnetic energy into thermal energy, and thermoelectric modules, temperature control over sample materials within the process chambers of a device located on the base plate may be effected in a variety of manners.

In one exemplary method of using sample processing devices of the present invention, it may be advantageous to provide DNA primers and probes in the process chambers during manufacturing of the sample processing devices. A DNA target sample could then be introduced into the process chambers to conduct PCR amplification of the DNA target. The target sample may include, e.g., target DNA, buffer and polymerase enzyme.

After the target sample has been distributed to the process chambers (containing the pre-loaded primers and probes), the temperature of the materials in each of the process chambers can be raised to a selected base temperature (e.g., 60° C.) to begin the PCR amplification. As the sample processing device rotates, a laser or other electromagnetic energy source can be used to raise the temperature of the sample materials in each of the process chambers to an upper target temperature at which, e.g., denaturing of the DNA occurs.

After reaching the target temperature, the sample materials are brought back down to the base temperature. In the methods of the present invention, the base temperature can be reached through convective cooling as the device rotates. That convective cooling alone, or in connection with conductive cooling using a base plate, impinging fluid jets, etc., preferably provides for rapid cooling of the sample materials, followed by rapid heating back up to the target temperature. The rapid heating and cooling is advantageous in that a desired number of thermal cycles can be completed in a relatively short period of time.

Sample processing devices of the present invention with process arrays such as those illustrated in, e.g., FIGS. 1–3, may be used to provide integrated processing of starting sample materials by, e.g., amplification of a starting sample material within a process array on the device. Each of the process arrays may include a number of process chambers that are preferably arranged on the device such that centrifugal forces can move fluids sequentially from chamber to chamber. The process chambers within each of the process arrays are in fluid communication using channels or other conduits that may, in some embodiments, include valve structures to control the movement as desired. Further, the input chambers and/or the output chambers of the process arrays are arranged in a rectilinear grid array such that automated loading and/or unloading of the chambers using conventional microtiter plate robotic pipetting equipment may be performed. Further, monitoring or detection of materials in the output chambers may also be performed using convention microtiter plate-based detection systems and methods.

Figure 10:
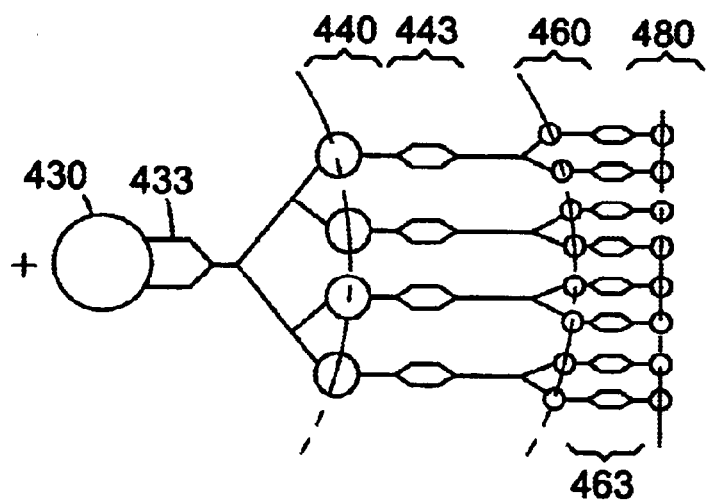
FIG. 10 is a schematic diagram of one process array that may be used to provide integrated processing of starting sample materials by, e.g., PCR amplification and Sanger sequencing on a single sample processing device.

One example of an integrated process that can be performed in a process array on a sample processing device of the present invention is schematically illustrated in FIG. 10 where an input chamber 430 is provided to receive, e.g., a starting sample material. The process array and one illustrative method of using the array will be described below. The illustrative method involves PCR amplification, followed by Sanger sequencing to obtain a desired end product. This combination of processes is, however, intended to be illustrative only and should not be construed as limiting the present invention.

Starting sample material, e.g., lysed blood cells, is provided in the input chamber 430. A filter 433 is preferably provided to filter the starting sample material as it moves from the input chamber 430 to the primary process chambers 440. The filter 433 is, however, optional and may not be required depending on the properties of the starting sample material.

The primary process chambers 440 may preferably include suitable PCR primers as supplied, e.g., dried down in each of the chambers 440. Each of the primary process chambers 440 may include the same primer or different primers depending on the nature of the investigation being performed on the starting sample material. One alternative to providing the primers in the primary process chambers 440 before loading the sample is to add a suitable primer to the input chamber 430 with the starting sample material (provided that the primer is capable of passing through the filter 433, if present).

After locating the starting sample material and any required primers in the primary process chambers 440, the materials in the process chambers 440 are thermally cycled under conditions suitable for PCR amplification of the selected genetic material.

After completion of the PCR amplification process, the materials in each of the primary process chambers 440 may be moved through another filter chamber 443 (one filter chamber 443 for each process chamber 440) to remove unwanted materials from the amplified materials, e.g., PCR primers, unwanted materials in the starting sample that were not removed by filter 433, etc. The filter chambers 443 may, for example, contain size exclusion substances, such as permeation gels, beads, etc. (e.g., MicroSpin or Sephadex available from Amersham Pharmacia Biotech AB, Uppsala, Sweden).

After clean-up of the sample materials in the filter chambers 443, the filtered PCR amplification products from each of the primary process chambers 440 are moved into a pair of multiplexed secondary process chambers 460 for, e.g., Sanger sequencing of the genetic materials amplified in the primary process chambers 440 through appropriate control of the thermal conditions encountered in secondary process chambers 460.

After the desired processing has been performed in the secondary process chambers 460, the processed material (Sanger sequenced sample material if that is the process performed in the secondary process chambers 460) is moved from each of the secondary process chambers 460 through another set of filter chambers 463 to remove, e.g., dyes or other unwanted materials from the product of the secondary process chambers 460. The filtered product is then moved from the filter chambers 463 into output chambers 480 where it can be removed.

As with the process arrays illustrated in FIGS. 1–5, it is also preferred that process arrays such as the array illustrated in FIG. 10 be arranged such that the primary process chambers 440 and the secondary process chambers 460 are arranged in circular arcs such that rotation of the device containing the process chambers moves the chambers about a circle. In addition, one or both of the input chambers 430 and the output chambers 480 are arranged in rectilinear grid arrays, such that loading, unloading, and/or detection of materials in those chambers may be performed using equipment designed to process devices providing materials arranged in rectilinear grid arrays, e.g., microtiter plates, etc.

A variety of advantages of the integrated process chamber array illustrated in FIG. 10 stem from the ability to move from a raw starting sample material to an isolated sequenced product in a single sample processing device. Among those advantages are reductions in the number physical transfers (by pipetting, etc.) that can be problematic when working with small volumes of materials. Another advantage is that multiple parallel processes can be simultaneously performed, providing potential improvements in confidence levels regarding the accuracy of the process results. In addition, there may be an enhanced level of control in ensuring that the process chambers see the same conditions with respect to, e.g., thermal cycling, etc.

Figure 11:
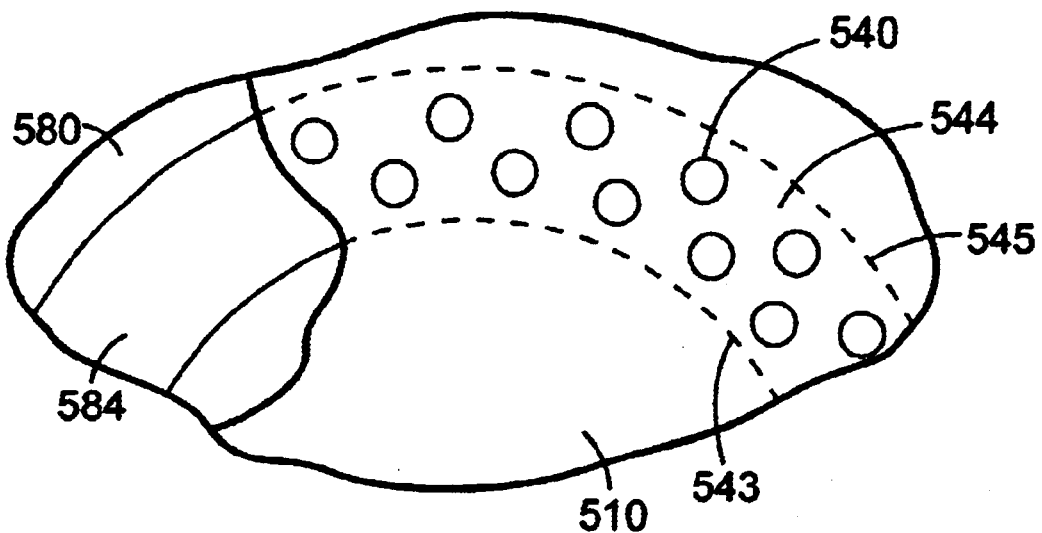
FIG. 11 depicts a portion of one sample processing device including process chambers located within a circular arc having a radial width.

FIG. 11 illustrates another optional feature of the sample processing devices of the present invention. The feature illustrated in FIG. 11 relates to the circular arc in which the process chambers 540 are arranged on the sample processing device 510. The circular arcs defined by the process chambers described thus far have a uniform radius as measured relative to the centers of their respective devices. FIG. 11, which depicts only a portion of one sample processing device 510, includes process chambers 540 arranged within a circular arc 544 having a radial width, i.e., the circular arc 544 has an inner edge 543 and an outer edge 545. This arrangement may allow for a larger number of process chambers 540 by increasing the process chamber density within the circular arc 544. Where the circular arc 544 has a radial width as depicted in FIG. 11, it will be understood that any process chamber circle formed by two or more circular arcs may be alternatively be described as an annular ring.

This arrangement may be particularly beneficial when used with an underlying thermal structure 584 in base plate 580 As depicted in FIG. 11, the thermal structure 584 may itself have a radial width. The circular arc 544 occupied by the process chambers 540 is, however, preferably located within the bounds of the underlying thermal structure 584 to avoid non-uniform thermal control of the process chambers 540.

Figure 12:
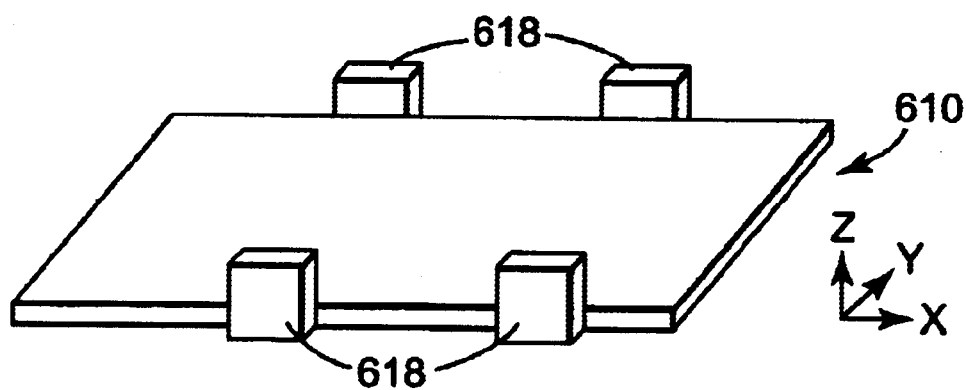
FIG. 12 is a perspective view of one sample processing device including handling tabs.

Another optional feature of sample processing devices according to the present invention is depicted in FIG. 12 and relates to automated handling and manipulation of the sample processing devices. It should be noted that this feature may not be coupled with a sample processing device that includes process chambers arranged in a circular array.

The optional feature illustrated in connection with the sample processing device 610 are the handling tabs 618 that provide height to the device 610. The tabs 618 preferably extend along the z-axis (see the reference axes in FIG. 12) to provide structure for, e.g., automated handling of the sample processing device 610. For example, a robotic gripper assembly (not shown) may be used to place and/or retrieve the sample processing device 610. Such a gripper assembly may function better if presented with a larger structure such as tabs 618 as opposed to the relatively smaller edge of the sample processing device 610 itself outside of the tabs 618.

The tabs 618 may be integral with the sample processing device 610 itself, e.g., they may be constructed by folding or molding the sample processing device 618. Alternatively, the tabs 618 may be added to the sample processing device 618 by any suitable technique or combination of techniques, e.g., adhesives, welding (thermal, chemical, etc.), heat sealing, etc.

Patents, patent applications, and publications disclosed herein are hereby incorporated by reference (in their entirety) as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A sample processing device comprising:
    a rectangular body comprising a pair of opposing major surfaces and a center, a first portion, and a second portion, wherein the first portion and the second portion are located on opposite sides of the center;
    a plurality of first process arrays located within the first portion of the body, each of the first process arrays comprising an input chamber, an output chamber, and a primary process chamber, the primary process chamber interconnected to, and located between, the input chamber and the output chamber, wherein the primary process chambers of the plurality of process arrays are arranged in a circular arc about the center of the body; and a plurality of second process arrays located within the second portion of the body, each of the second process arrays comprising an input chamber, an output chamber, and a primary process chamber located between the input chamber and the output chamber, wherein the primary process chambers of the plurality of second process arrays are arranged in a circular arc about the center of the body.

2. A device according to claim 1, wherein the circular arcs formed by the primary process chambers of the first process arrays and the second process arrays define a primary process chamber circle with a center located at the center of the body.

3. A device according to claim 1, wherein the input chambers of the plurality of first process arrays and the input chambers of the plurality of second process arrays are arranged in a rectilinear grid array.

4. A device according to claim 3, wherein the input chambers of the plurality of first process arrays are arranged along a first straight line and the input chambers of the plurality of second process arrays are arranged along a second straight line, and further wherein the first straight line is parallel to the second straight line.

5. A device according to claim 1, wherein the output chambers of the plurality of first process arrays are arranged in a rectilinear grid array, and further wherein the output chambers of the plurality of second process arrays are arranged in a rectilinear grid array.

6. A device according to claim 1, wherein the input chambers of at least two of the first process arrays comprise a common input chamber.

7. A device according to claim 1, wherein the input chambers of all of the plurality of first process arrays comprise a common input chamber.

8. A device according to claim 1, the device further comprising:
   a secondary process chamber located between the primary process chamber and the output chamber of each of the first process arrays, wherein the secondary process chambers of the first process arrays are arranged in a circular arc about the center of the body; and
   a secondary process chamber located between the primary process chamber and the output chamber of each of the second process arrays, wherein the secondary process chambers of the second process arrays are arranged in a circular arc about the center of the body.

9. A device according to claim 8, wherein the circular arcs formed by the secondary process chambers of the first process arrays and the second process arrays define a secondary process chamber circle with a center located at the center of the body.

10. A sample processing device comprising:
    a rectangular body comprising a center, a first portion, and a second portion, wherein the first portion and the second portion are located on opposite sides of the center;
    a plurality of first process arrays located within the first portion of the body, each of the first process arrays comprising an input chamber, an output chamber, and a primary process chamber, the primary process chamber interconnected to, and located between, the input chamber and the output chamber, wherein the primary process chambers of the plurality of process arrays are arranged in a circular arc about the center of the body; and
    a plurality of second process arrays located within the second portion of the body, each of the second process arrays comprising an input chamber, an output chamber, and a primary process chamber located between the input chamber and the output chamber, wherein the primary process chambers of the plurality of second process arrays are arranged in a circular arc about the center of the body;
    wherein the input chambers of the plurality of first process arrays and the input chambers of the plurality of second process arrays are arranged in rectilinear grid array;
    and wherein the output chambers of the first process arrays of the plurality of first process arrays are arranged in a rectilinear grid array,
    and further wherein the output chambers of the second process arrays of the plurality of second process arrays are arranged in a rectilinear grid array.

11. A device according to claim 10, wherein the circular arcs formed by the primary process chambers of the first process arrays and the second process arrays define a primary process chamber circle with a center located at the center of the body.

12. A device according to claim 10, wherein the input chambers of at least two of the first process arrays comprise a common input chamber.

13. A device according to claim 10, wherein the input chambers of all of the plurality of tint process arrays comprise a common input chamber.

14. A device according to claim 10, the device further comprising:
    a secondary process chamber located between the primary process chamber and the output chamber of each of the first process arrays, wherein the secondary process chambers of the first process arrays are arranged in a circular arc about the center of the body; and
    a secondary process chamber located between the primary process chamber and the output chamber of each of the second process rays, wherein the secondary process chambers of the second process arrays are arranged in a circular arc about the center of the body.

15. A device according to claim 14, wherein the circular arcs formed by the secondary process chambers of the first process arrays and the second process arrays define a secondary process chamber circle with a center located at the center of the body.

16. A sample processing device comprising:
    a body comprising a center, a first portion, and a second portion, wherein the first portion and the second portion are located on opposite sides of the center;
    a plurality of first process arrays located within the first portion of the body, each of the first process arrays comprising an input chamber, an output chamber, and a primary process chamber, the primary process chamber interconnected to, and located between the input chamber and the output chamber, wherein the primary process chambers of the plurality of process arrays are arranged in a circular arc about the center of the body, and further wherein the output chambers of the plurality of first process arrays are arranged in a rectilinear grid array; and a plurality of second process arrays located within the second portion of the body, each of the second process arrays comprising an input chamber, an output chamber, and a primary process chamber located between the input chamber and the output chamber, wherein the primary process chambers of die plurality of second process arrays are arranged in a circular arc about the center of the body, and further wherein the output chambers of the plurality of second process arrays are arranged in a rectilinear grid array.

17. A device according to claim 16, wherein the circular arcs formed by the primary process chambers of the first process arrays and the second process arrays define a primary process chamber circle with a center located at the center of the body.

18. A device according to claim 16, wherein the input chambers of the plurality of first process arrays and the input chambers of the plurality of second process arrays are arranged in a rectilinear grid array.

19. A device according to claim 18, wherein the input chambers of the plurality of first process arrays are arranged along a first straight line and the input chambers of the plurality of second process arrays are arranged along a second straight line, and further wherein the first straight line is parallel to the second straight line.

20. A device according to claim 16, wherein the input chambers of at least two of the first process arrays comprise a common input chamber.

21. A device according to claim 16, wherein the input chambers of all of the plurality of first process arrays comprise a common input chamber.

22. A device according to claim 16, the device further comprising:
  a secondary process chamber located between the primary process chamber and the output chamber of each of the first process arrays, wherein the secondary process chambers of the first process arrays are arranged in a circular arc about the center of the body; and
  a secondary process chamber located between the primary process chamber and the output chamber of each of the second process arrays, wherein the secondary process chambers of the second process arrays are arranged in a circular arc about the center of the body.

23. A device according to claim 22, wherein the circular arcs formed by the secondary process chambers of the first process arrays and the second process arrays define a secondary process chamber circle with a center located at the center of the body.

24. A sample processing device comprising:
  a body comprising a center, a first portion, and a second portion, wherein the first portion and the second portion are located on opposite sides of the center;
  a plurality of first process arrays located within the first portion of the body, each of the first process arrays comprising an input chamber, an output chamber, and a primary process chamber, the primary process chamber interconnected to, and located between, the input chamber and the output chamber, wherein the primary process chambers of the plurality of process arrays are ranged in a circular arc about the center of the body, and further wherein the input chambers of the plurality of first process arrays are arranged in a rectilinear grid array; and
  a plurality of second process arrays located within the second portion of the body, each of the second process arrays comprising an input chamber, an output chamber, and a primary process chamber located between the input chamber and the output chamber, wherein the primary process chambers of the plurality of second process arrays are arranged in a circular arc about the center of the body, and further wherein the input chambers of the plurality of second process arrays are arranged in a rectilinear grid array.

25. A device according to claim 24, wherein the circular arcs formed by the primary process chambers of the first process arrays and the second process arrays define a primary process chamber circle with a center located at the center of the body.

26. A device according to claim 24, wherein the input chambers of the plurality of first process arrays are arranged along a first straight line and the input chambers of the plurality of second process arrays are arranged along a second straight line, and further wherein the first straight line is parallel to the second straight line.

27. A device according to claim 24, wherein the input chambers of at least two of the first process arrays comprise a common input chamber.

28. A device according to claim 24, the device further comprising:
  a secondary process chamber located between the primary process chamber and the output chamber of each of the first process arrays, wherein the secondary process chambers of the first process arrays are arranged in a circular arc about the center of the body; and
  a secondary process chamber located between the primary process chamber and the output chamber of each of the second process arrays, wherein the secondary process chambers of the second process arrays are arranged in a circular arc about the center of the body.

29. A device according to claim 28, wherein the circular arcs formed by the secondary process chambers of the first process arrays and the second process arrays define a secondary process chamber circle with a center located at the center of the body.

* * * * *

UNITED STATES PATENT AND TRADEMARK OFFICE
CERTIFICATE OF CORRECTION

PATENT NO. : 6,720,187 B2
DATED : April 13, 2004
INVENTOR(S) : Bedingham, William It is certified that error appears in the above-identified patent and that said Letters Patent is hereby corrected as shown below:

Column 18,
Line 20, delete "eg." and insert -- e.g. --, therefor.

Column 24,
Line 33, delete "tint" and insert -- first --, therefor.
Line 44, delete "rays" and insert -- arrays --, therefor.
Line 60, after "between" insert -- , --.

Column 25,
Line 6, delete "die" and insert -- the --, therefor.

Column 26,
Line 6, delete "ranged" and insert -- arranged --, therefor.

Signed and Sealed this

Twenty-first Day of June, 2005

JON W. DUDAS
*Director of the United States Patent and Trademark Office*